United States Patent

Glynn et al.

[11] Patent Number: 5,297,554
[45] Date of Patent: Mar. 29, 1994

[54] DEVICE FOR USE IN REAL-TIME MONITORING OF HUMAN OR ANIMAL BODILY FUNCTION

[76] Inventors: Christopher J. Glynn, Bridge Farmhouse, Appleford, Oxon OX14 4NU, United Kingdom; Adrian R. Hill, Brewers, Sheepstead, Abingdon, Oxon, OX13 6QG, United Kingdom

[21] Appl. No.: 768,645
[22] PCT Filed: Apr. 26, 1990
[86] PCT No.: PCT/GB90/00648
 § 371 Date: Sep. 27, 1991
 § 102(e) Date: Sep. 27, 1991
[87] PCT Pub. No.: WO90/12534
 PCT Pub. Date: Nov. 1, 1990

[30] Foreign Application Priority Data

Apr. 26, 1989 [GB] United Kingdom ............... 8909491

[51] Int. Cl.⁵ ............... A61B 6/00; A61B 5/00; A61B 3/14
[52] U.S. Cl. ............... 128/665; 128/633; 351/206
[58] Field of Search ............... 128/665, 632.3, 666; 351/206, 219

[56] References Cited

U.S. PATENT DOCUMENTS

| | | |
|---|---|---|
| 3,036,568 | 5/1962 | Stark ............... 128/665 X |
| 4,007,980 | 2/1977 | Bracher et al. . |
| 4,166,695 | 9/1979 | Hill et al. ............... 128/666 X |
| 4,402,325 | 9/1983 | Dudragne . |
| 4,412,543 | 11/1983 | Vassiliadis et al. ............... 128/665 X |
| 4,461,303 | 7/1984 | Refojo et al. . |
| 4,569,354 | 2/1986 | Shapiro et al. ............... 128/665 |
| 4,597,392 | 7/1986 | Opitz et al. ............... 128/665 X |
| 4,699,482 | 10/1987 | Utsugi . |
| 4,836,207 | 6/1989 | Bursell et al. ............... 128/665 X |
| 4,883,061 | 11/1989 | Zeimer ............... 128/665 |
| 4,957,113 | 9/1990 | Benedek ............... 128/665 |

FOREIGN PATENT DOCUMENTS 8901762 3/1989 World Int. Prop. O. ......... 128/665

Primary Examiner—Randall L. Green
Assistant Examiner—Elizabeth M. Burke
Attorney, Agent, or Firm—Davis, Bujold & Streck

[57] ABSTRACT

The device comprises a scleral contact lens (1) for locating and supporting the device on the eye and has an optical system with at least one discrete light source, e.g. an optical fiber (9) or a light emitting diode, and at least one discrete light receiver, e.g. an optical fiber (10) or a photodetector, mounted within a carrier (6) on the scleral contact lens (1). The device may be used for spectrophotometric analysis of the retina (31) enabling it to be used in a wide variety of diagnostic and monitoring techniques. In a further arrangement (FIGS. 5 and 6) the device may be used to provide infra-red pupillometry. Further sensing devices may also be provided on the contact lens (1).

23 Claims, 5 Drawing Sheets

DEVICE FOR USE IN REAL-TIME MONITORING OF HUMAN OR ANIMAL BODILY FUNCTION

TECHNICAL FIELD

This invention relates to a device for use in real-time monitoring of human or animal bodily functions in vivo and more particularly to a device for monitoring these functions via the eye.

It is necessary to monitor the condition of a human or animal body in many different situations. One particularly important time is during anaesthesia when surgery or other treatment is being carried out. The status and condition of the body is assessed by monitoring the level or variation of a number of parameters such as pulse rate, blood pressure, temperature etc. A range of instruments and devices are available to assist a doctor in monitoring the condition of a patient in these situations and some of those available with reference to anaesthesia will be described below.

BACKGROUND ART

The most important function to monitor is oxygen supply to the brain, e.g. for example during anaesthesia. The measurement of this is known as pulse oximetry. The brain can only survive on oxygen and glucose, i.e. by aerobic metabolism, whereas most other tissues can survive for a period without oxygen, is by anaerobic metabolism. The oxygen supply is a function of delivery, i.e. cardiac output which governs all blood flow, and the amount of oxygen available in the blood, which is governed by the $O_2$ haemoglobin dissociation curve.

The blood flow is assessed by monitoring blood pressure and by assuming the resistance is constant, so the pressure is directly related to flow (Ohm's law) and by pulse rate which is generally measured with an electrocardiogram (ECG) and/or a pulse oximeter. The amount of oxygen available is measured with a pulse oximeter which calculates the percentage saturation of the haemoglobin by using one, two or three monochromatic light sources. The amount of light passing through tissue of the body is recorded to determine the quantity of light absorbed by the haemoglobin. These devices usually measure the saturation in the periphery, e.g. in the toe, finger or ear, and this is assumed to be related to the oxygen saturation of blood delivered centrally to the brain.

The major limitation of pulse oximetry is that the measures are of peripheral and not central blood flow. Other limitations of pulse oximetry are;

(i) The calculations are based on the Beer Lambert law and it is known that due to the scattering of light by skin tissue and other structures the application of this law is not valid under these conditions.

(ii) The wavelengths of light used are usually determined by the available light emitting diodes and these may not be ideal. Existing machines use only one, two or three wavelengths which further limits the accuracy of the oxygen saturation calculation.

(iii) Ambient light may interfere with the signal detection and hence reduce its sensitivity.

(iv) The spectral absorbance of the tissue through which the light is transmitted affects the results, e.g. with non-Caucasians.

(v) Other chemicals normally found in the blood, e.g. bilirubin, may also interfere with the transmission of the light and have an unknown influence on the results.

The electro-retinogram (ERG) is also used to assess the function of the retina. This device uses a contact lens provided with a circular electrode for detecting electrical activity of the retina. Stimulation is provided by an external light source directed into the eye.

Contact lenses provided with mirrors or lenses have also been used for observing the angle of the anterior chamber and the peripheral fundus of the eye. A high-negative-powered contact lens has also been used to assist observation of the retinal fundus during opthalmoscopy and a telescopic device has been used on a contact lens for the study of stabilised retinal images.

The size of the pupil may be used as a clinical guide during anaesthesia and infra-red pupillometry has been described as a method of assessing various aspects of visual functions. In this method, an external infra-red camera is used to measure the size of the pupil without influencing its size. The use of a train of four electrical pulses to stimulate a muscle to assess neuro-muscular blockage during anaesthesia has also been described.

Visual evoked potentials (VEP), have also been used to monitor the condition of a patient during anaesthesia and at other times. The potentials are measured by recording changes in the electrical activity of the brain following a measured visual stimulus or series of measured visual stimuli. An electro-cardiogram (ECG) is used to measure the electrical activity of the heart and as such provides a measure of heart-rate, heart rhythm, muscular contraction and, indirectly, oxygen supply to the muscle.

One of the aims of the present invention is to provide a device for non-invasive, real time monitoring of cardiovascular, respiratory, neuro-muscular and other bodily functions whilst avoiding some of the disadvantages of the prior art.

DISCLOSURE OF INVENTION

According to a first aspect of the invention there is provided a device for use in real-time monitoring of human or animal bodily functions in vivo comprising: a scleral contact lens for locating and supporting the device on the eye; and a first optical system supported by the contact lens having at least one discrete light input means and at least one discrete light receiving means, characterised in that the arrangement is such that, in use, the light input means is arranged to direct light through the contact lens and the pupil of the eye so as to illuminate the retina of the eye substantially independently of the size of the pupil and the light receiving means is positioned so as to receive light returning through the contact lens directly from that portion of the retina which is illuminated directly by the light input means.

A preferred form of the device avoids the shortcomings described above of conventional pulse oximetry, as well as providing means for monitoring other bodily functions, by using a first optical system for visible, ultra-violet, and infra-red spectrophotometric or fluospectrophotometric analysis of retinal blood flow.

Another preferred form of the device enables the size of the pupil to be monitored, even when the eyelids are substantially closed, by using a second optical system for infra-red pupillometry, e.g. during anaesthesia.

According to a second aspect of the invention there is provided a disposable component of a device for real-time monitoring of human or animal bodily functions in vivo, the component comprising a scleral contact lens for locating and supporting the device on the eye and mounting means on the contact lens adapted for detachably mounting and supporting an optical system on the lens in such a manner that, when mounted thereon, the optical system is positioned to direct light through the contact lens and the pupil of the eye so as to illuminate the retina of the eye substantially independently of pupil size and to receive light returning through the contact lens from that portion of the retina illuminated thereby.

According to another aspect of the invention there is provided a device for use in real-time monitoring of human or animal bodily functions in vivo comprising: a scleral contact lens for locating and supporting the device on the eye and an optical system supported by the contact lens arranged to direct light towards the eye and to receive light reflected from the iris of the eye, characterised in that the optical system comprises an array of discrete light input means for providing light for directing towards the eye at a series of different distances from the optical axis and an array of discrete light receiving means for receiving light reflected from the iris of the eye at a series of different distances from the optical axis.

According to a further aspect of the invention there is provided a method of real-time monitoring human or animal bodily functions in vivo using a device as described above.

Other preferred features of the invention will be apparent from the following description and the subsidiary claims of the specification.

BRIEF DESCRIPTION OF DRAWINGS

The invention will now be further described, merely by way of example, with reference to the accompanying drawings, in which.

BEST MODE OF CARRYING OUT THE INVENTION

Figure 1A:
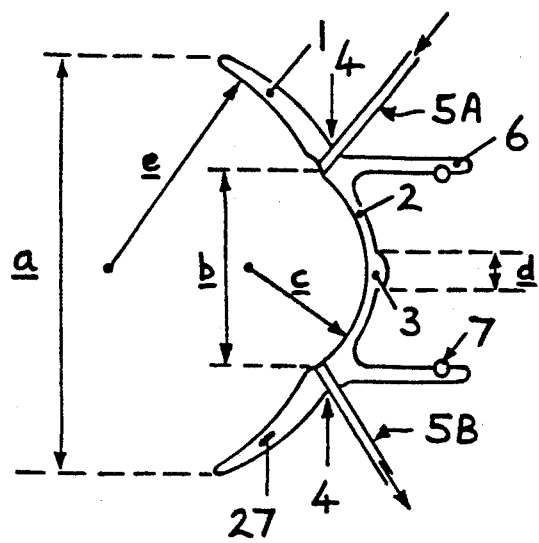
FIG. 1A is a cross-sectional view of a special adaptation of a scleral contact lens used in an embodiment of the invention and FIG. 1B is a perspective view thereof.

The device to be described uses a scleral contact lens as a vehicle for an optical system to monitor human or animal bodily functions via the eye and is based on the realisation that since the pre-retinal structures of the eye are designed to transmit light, it is well suited to optical methods of examination. Furthermore, the eye provides a more direct method of assessing the condition of the brain than some of the prior art methods described. This is because the major blood supply to the eye via the ophthalmic artery is a branch of the internal carotid artery. The eye, therefore, is sometimes aptly referred to as the 'window' of the brain. Preferred forms of the device enable several different functions or parameters to be monitored, both in conjunction and independently of the optical system of the device, using the same equipment.

As mentioned above, the device offers, a non-invasive method of real-time monitoring of the cardiovasuclar, respiratory and neuro-muscular functions in man. In addition, it offers a method of an vivo measurement of the various cellular and chemical constituents found normally in blood. It is also possible to measure foreign chemicals and their metabolites, e.g. drugs, once their individual absorbance/reflectance spectrum has been identified.

Before the device is described in detail, some of the different functions it can be used to perform will be briefly described:

1. Measurement of the amount and change of any or all cells and chemicals found in the blood using light, in the visible, infra-red and ultra-violet range to detect the unique absorbance/reflectance spectrum of each cell or chemical by spectrophotometry. This applies to naturally occurring substances as well as foreign substances.

2. Measurement of changes in the oxygen saturation of haemoglobin by spectrophotometry to assess oxygen delivery to the retina and so provide a measure of oxygen delivery to the brain. Similarly, changes from one haemoglobin to another, e.g. oxyhaemoglobin to reduced haemoglobin, can be measured as well as percentage changes in abnormal haemoglobin such as Hbs, the cause of sickle cell disease.

3. Measurement of arterial carbon dioxide tension using the reflectance of infra-red light from blood vessels in the retina.

4. Measurement of retinal blood flow (which is related to cardiac output and to cerebral blood flow) using spectrophotometry to measure the transport of specific substances in the blood.

5. Measurement of the pulse rate by detecting blood volume changes consequent to changes in the width of blood vessels on the retina or the cycles of oxygen saturation of haemoglobin during diastole and systole by spectrophotometry.

6. Measurement of the depth of anaesthesia and/or level of consciousness by infra-red pupillometry.

7. Measurement of pressure changes in the eye to measure or monitor arterial blood pressure and/or pulse rate.

8. Measurement of the change in pH of artificial tears used in this pressure measurement as a measure of the pH changes in the blood.

9. Measurement of the increase in volume of these artificial tears as a measure of the depth of anaesthesia.

10. Measurement of integrative retinal activity to measure the electrical activity of the retina to assess the depth of anaesthesia and the level of consciousness by using the device as part of an electroretinogram.

11. Measurement of changes in visual evoked potentials to assess the depth of anaesthesia and the level of consciousness.

12. Measurement of electrical changes recorded by the electrodes used for measurement of the integrative retinal activity and visual evoked potentials to monitor the electrical activity of the heart and to record an ECG.

13. Measurement of neuromuscular blockade during anaesthesia by use of electromyograms (EMGs) of all four recti eye muscles.

14. Measurement of neuro-muscular blockade during anaesthesia by electrical stimulation of the lateral rectus muscle, with train of four stimulation, and using infrared pupillometry to record the movement or lack of movement of the eye.

15. Measurement of body temperature using either a thermistor (thermocouple) or infra-red sensor provided on the device.

16. Measurement of biochemical reactions and cellular respiration in the retina.

The expression 'human or animal bodily functions' used in this specification is intended to include all the different functions mentioned above and the monitoring of any substances and changes in the blood of the retina and any biochemical (organic or inorganic) changes in the cells of the retina.

It should also be noted that it is possible with the device to monitor in real time any one or all of these functions separately or together, either intermittently or continuously.

The term 'light' used in this specification is intended to include visible wavelengths and other, non-visible wavelengths such as infra-red and ultra-violet light.

The device will now be described in more detail with reference to the accompanying drawings. The scleral contact lens will first be described and then the components relating to the different functions mentioned above which can be grouped under the headings spectrophotometry, pupillometry, fluid measurements, electrophysiology and temperature measurements. Finally, the analysis and display equipment used with the device will be briefly described.

THE CONTACT LENS

A scleral contact lens 1 formed of polymethylmethacrylate (PMMA) or other suitable sterilisable material is preferably used. The scleral contact lens 1 is designed to fit onto the sclera and bulbar conjunctive of the eye so if the eye moves the contact lens 1 moves with it. The scleral contact lens was first used in 1888 as a protective device for the cornea and there have been various clinical and therapeutic applications since then, such as those mentioned above.

To protect the cornea, sclera and bulbar conjunctive, a hard haptic scleral contact lens may be ensheathed in a low or high water content, hydrophilic material such as that used in the manufacture of soft contact lenses. Such a sheathing also allows the contact lens to be made of other materials as only the sheathing material is in contact with the eye.

Figure 1B:
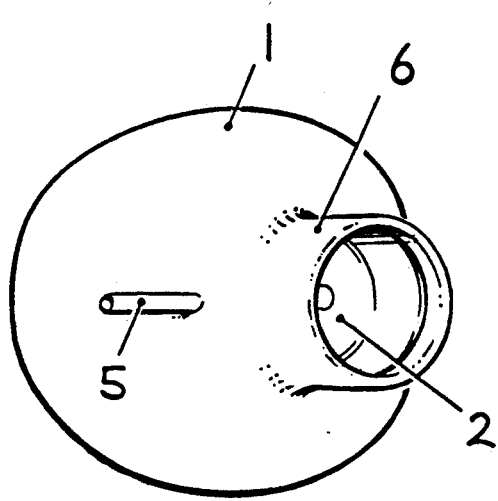

The scleral contact lens shown in FIG. 1 has a central optical portion 2 provided with a converging lens for focussing light through and substantially in the plane of the pupil so as to illuminate the retina of the eye. FIG. 1 shows the lens 1 and the central optical portion 2 (also known as the corneal portion). The optical portion 2 has a smaller radius of curvature than the remainder of the lens (the haptic portion). The radius c of the optical portion 2 is made shorter than the 95th percentile of human cornea and is therefore typically around 6.5 mm. When the lens 1 is fitted to the eye, the optical portion 2 is thus raised from the cornea. The diameter b of the optical portion 2 is typically 13 mm or more.

The back haptic radius e of the scleral contact lens 1 is typically between 12 and 15 mm and the back haptic size a between 20 and 25 mm (vertically) with the horizontal size usually being 1 to 2 mm larger. A selection of three different size lenses 1 is usually provided to fit most human eyes.

At the centre of the optical portion 2 is a converging lens 3 in the form of a high powered positive lenticular with a diameter d of about 3 mm provided on a plano carrier. The optical axis of the lens 3 is substantially coincident with the optical axis of the eye.

Figure 2A:
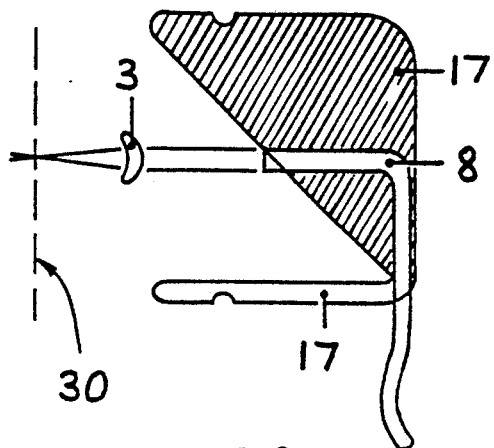
FIG. 2A is a cross-sectional view showing components of a first optical system used with the contact lens shown in FIG. 1 for spectrophotometry and FIG. 2B is a perspective view thereof.

The lenticular 3 is arranged to focus collimated light in the plane of the pupil 30 for an average anterior chamber depth of 4 mm (see FIG. 2A) to produce an image of the illumination source (see below) substantially in the plane of the pupil. This is known as Maxwellian view. Illumination is thus provided along the optic axis of the eye and the lenticular 3 focusses the light substantially in the plane of the pupil 30. In this way, the retina is illuminated substantially independently of pupil size so the need to use a mydriatic to dilate the pupil is minimised.

As problems can be encountered with light reflected from the cornea if the illumination is directly along the optic axis, it may be preferable to provide the illumination slightly off axis or at a small angle thereto but, nevertheless, substantially along the optic axis. Alternatively, an anti-reflective coating may be applied to the surfaces of the optical components.

In the arrangement shown, the focal length of the lenticular 3 is around 5 mm, i.e. it has a strength of about 200 dioptres. As the optical portion 2 of the scleral contact lens 1 is raised from the cornea, it increases the distance between the lenticular 3 and the eye so avoiding the need for the lenticular to be of even higher power in order to focus light substantially in the plane of the pupil 30.

Between the optic and haptic portions of the contact lens 1 there is a transition curve where the two portions blend together. At this point a small (e.g. about 1 mm in diameter) fenestration or aperture 4 is provided (both medially and laterally) so that a fluid such as artificial tears may be passed through the lens 1 to the eye to prevent the cornea becoming dry beneath the lens. Artificial tears are provided along a tube or cannula 5A connected to one of the apertures 4 and a tube or cannula 5B connected to the other aperture 4 receives fluid returning from the eye.

In an alternative arrangement (not shown), the tubes 5A and 5B may be included within the wall thickness of a carrier 6 (see below) mounted on the contact lens 1 with countersunk apertures on the corneal side of the lens 1.

In either arrangement, the tubes 5A and 5B are preferably connected in a closed system (not shown), e.g. by flexible tubing leading to other devices (see below).

Extending from the scleral contact lens 1 is a carrier 6 for receiving components of one or more optical systems such as those described below. A rubber O-ring locking device 7 or other attachment means is provided for detachably securing these within the carrier 6. These further components will be described below in relation to the different functions of the device.

Both the carrier 6 and the haptic portion of the contact lens 1 are preferably provided with an opaque lamination, or manufactured from opaque material such as black perspex, to prevent light from outside the device interfering with its function.

The scleral contact lens 1 and carrier 6 may be formed of relatively inexpensive material so they can be disposed of after use. Components of the optical system can thus be detached from the carrier 6 as described above and then installed in the carrier 6 of a new contact lens unit to be used with another patient.

Figure 2B:
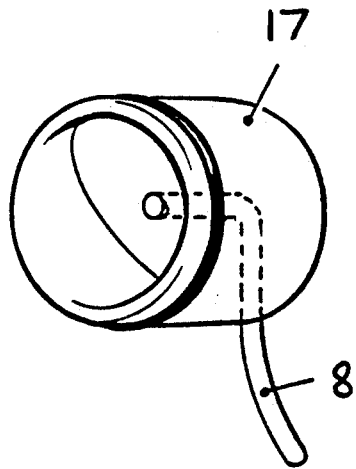

SPECTROPHOTOMETRY AND FLUO-SPECTROPHOTOMETRY for measurements involving illumination of the retina and the detection of light returning therefrom to determine the absorbance/reflectance spectrum of the retinal blood supply, a first optical system comprising optical components such as those shown in FIG. 2 (and FIGS. 8 to 11) is used within the carrier 6. The arrangement shown in FIG. 2 comprises a support 17 which fits within the carrier 6 and which houses a coherent or semi-coherent fibre optic bundle 8 positioned in front of the lenticular 3 and directed towards the pupil of the eye along the optic axis thereof.

Figure 4:
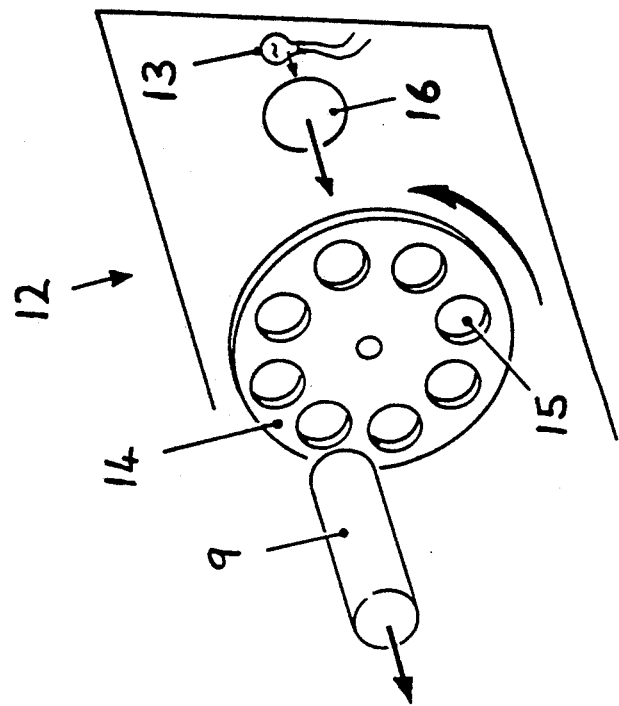
FIGS. 3 and 4 are perspective views of further parts of the first optical system shown in FIG. 2.
Figure 3:
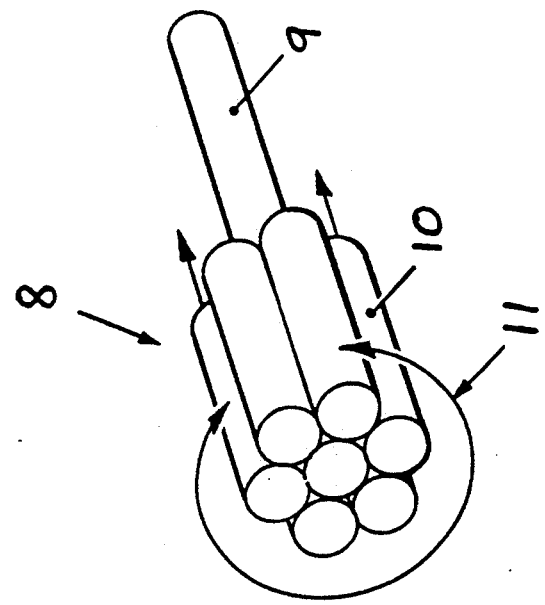

FIGS. 3 and 4 show the parts of this optical system in more detail. The fibre optic bundle 8 comprises a central illumination fibre or fibres 9 for directing light through the lenticular 3 and one or more paraxial receiving fibres 10 grouped around the central fibre 9 for receiving light returning from the retina. A light absorbent outer sheathing 11 is provided around the fibres to prevent interference from ambient stray light and to prevent light loss from the fibres. The illumination fibres 9 are also masked from the receiving fibres 10. The central fibre 9 thus provides a discrete light input means and the fibres 10 a plurality of discrete light receiving means.

A light source is provided remote from the device at the other end of the illumination fibre 9 and preferably comprises a halogen bulb 13 positioned behind a rotatable wheel 14 provided with a range of different, monochromatic interference filters 15 with a condenser lens 16 between the bulb 13 and the wheel 14. Thus, by positioning the appropriate filter 15 in front of the beam of light from the bulb 13, light of a selected wavelength is transmitted through the illumination fibre 9 to the lenticular 3 which focusses the light through the pupil of the eye to illuminate the retinal fundus. Different wavelengths can be used in succession by rotation of the filter wheel 14.

Alternatively, the light source may be provided either by reflected, coherent monochromatic light (e.g. from a laser) or selected light emitting diodes.

Light returning from the retina passes out of the eye through the pupil, through the optical portion 2 of the contact lens 1 towards the ends of the receiving fibres 10 which transmit the returning light to a remote light-sensing means, e.g. a photo-multiplier (not shown), provided at the other ends of the receiving fibres 10, to determine the intensity of the returning light. Thus, by using a series of different wavelength selective filters 15, the absorbance/reflectance characteristic of the retina and its blood supply can be determined.

The first optical system may be arranged in a variety of ways to provide spectrophotometry of the retina. When optical fibre are used, as described above, the illumination may be provided by means of spectral light emitting diodes (not shown), e.g. emitting red, green, yellow and blue light. Alternatively, white light may be used to illuminate the retina and the returning light passed through monochromatic filters before being passed to the light detector. The fibres themselves could also act as filters if they are formed of selectively, spectrally absorbing material. It would also be possible to monitor simultaneously the different wavelengths in the returning light.

In a further alternative, the wheel 14 may be replaced by a coloured liquid crystal charged couple device (CCD) for direct colorimetry. With white light illumination via the fibres 9, light returning from the eye is directed by the receiving fibres 10 onto the charged couple device. Ultra-violet and infra-red light sources may also be used.

In some cases, it may also be convenient for the same optical fibre or fibres to act as both light input means and light receiving means.

In a further alternative arrangement (not shown), a number of photodiodes (spectral light emitting diodes) or other discrete light emitting means of specified wavelengths may be carried by the device to provide a light source on the device and so avoid the need to use optical fibres. Such diodes may be mounted on a separate unit for insertion into the carrier 6 or mounted directly on a support attached to the scleral contact lens 1.

It is also possible to provide a photodetector (not shown) or other discrete light sensing means, carried by the device to provide a light receiver without the need for optical fibres. This may, for instance, be annular in shape and positioned on the optical portion 2 of the contact lens to receive light returning from the fundus of the eye.

The light source and light sensing means mounted in the device would be provided with electrical connections to enable them to be connected to a suitable power source and other electrical equipment. A wide variety of other optical systems using one or more discrete light input means and discrete light receiving means arranged to determine the absorbance/reflectance characteristic of light returned by the retina can be used and will be apparent to those skilled in the art.

The light input means and light receiving means, whether in the form of optical fibres or discrete device mounted on the device, are sufficiently small and lightweight to allow the device with its optical system to be supported on a patient's eye so avoiding the need to position and support heavy, bulky equipment in front of the eye. The device is therefore easy and convenient to use, particularly for continuous monitoring of a patient's condition, e.g. when anaesthetised.

Figure 8:
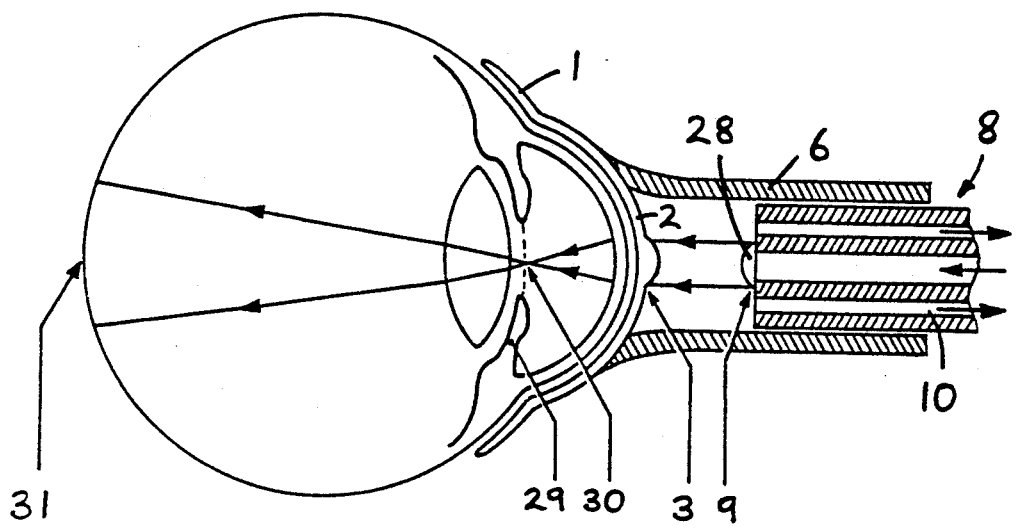
FIGS. 8, 9 and 10 are cross-sectional views showing the use of a scleral contact lens such as that shown in FIG. 1 on the eye and the optical paths of incident light in three different embodiments of the first optical system
Figure 9:
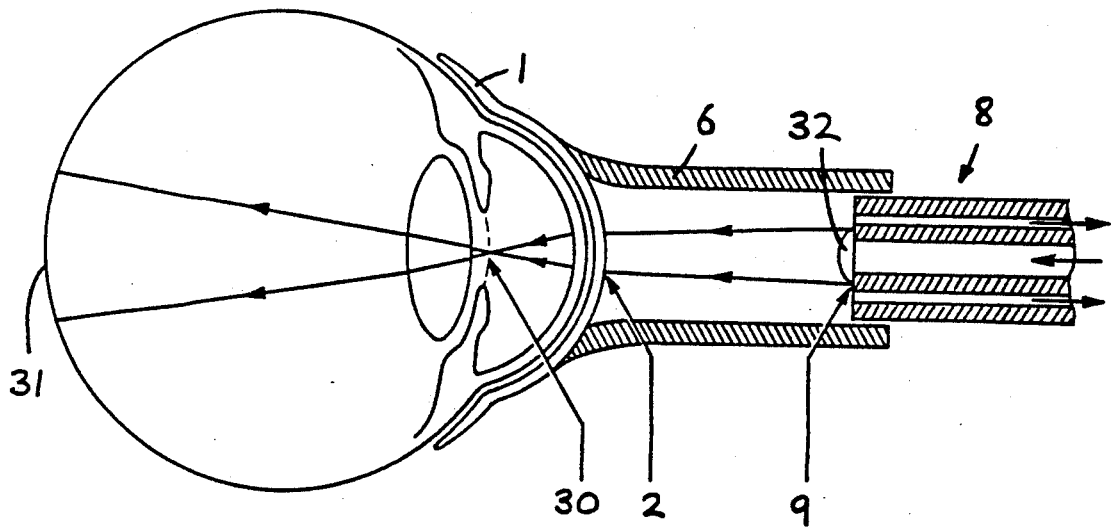
Figure 10:
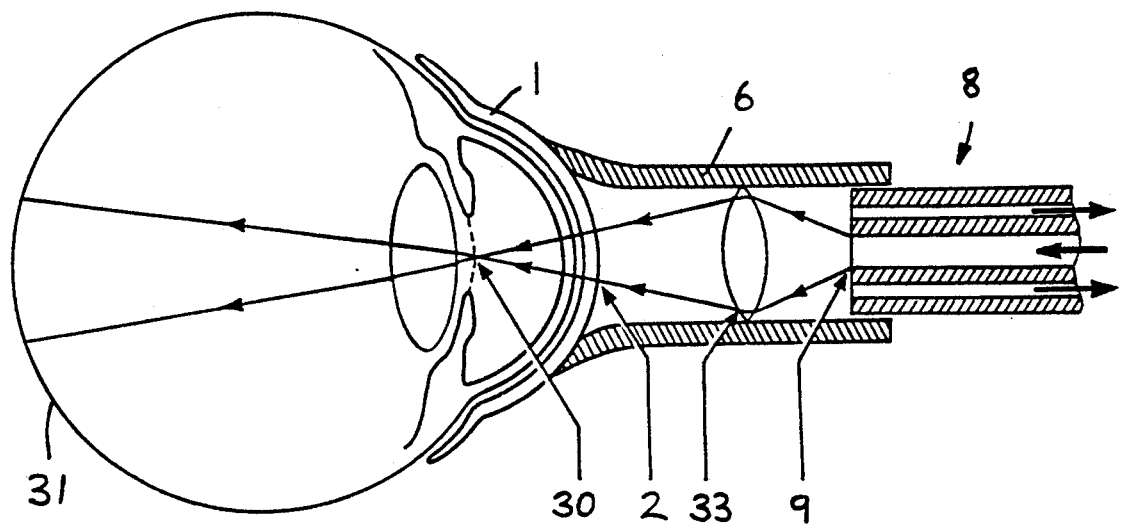

FIGS. 8, 9 and 10 show the use of the device described above in relation to the eye and illustrate different arrangements of the first optical system.

The device shown in FIG. 8 corresponds to that shown in FIGS. 1 and 2, but includes an additional converging lens 28 on the end of the central illumination optical fibre 9 as this helps provide an approximately collimated beam of light from the fibre 9 towards the lenticular 3. It also helps minimise the effect of unwanted reflections from stray light reaching the iris 29 through the optical portion 2 of the lens around the lenticular 3.

As shown in FIG. 8, the lenticular 3 focusses the light in the region of the eye's pupillary plane 30 (shown by dotted lines) so as to minimise the effect of pupil size on the level of illumination of the retinal area 31. The optical portion 2 of the scleral contact lens may have a smaller radius of curvature than the cornea (as shown in FIG. 1) or may have a similar radius of curvature to the cornea but not in contact therewith as shown in FIGS. 8 to 11. In either case, the optical effect of tears between the lens and the cornea will have little effect on the focussing of light in the plane of the pupil due to the depth of field of the lenticular 3 for the other lenses described below).

In a further arrangement (not shown), the contact lens may be shaped so that tear fluid between the lens and the cornea forms part of the optical system for focussing the light in the plane of the pupil or acts as the sole converging lens in the optical system.

In the arrangement shown in FIG. 9, a high powered converging lens 32 is provided on the end of the central illumination fibre 9 and replaces both the lenticular 3 and the converging lens 28 of the arrangement described above. The optical portion 2 of the contact lens may thus be of zero strength. The lens 32 produces a convergent beam of light which passes through the optical portion 2 of the contact lens 1 and is brought to a focus in the region of the eye's pupillary plane 30. The distance between the lens 32 and the contact lens 1 can be adjusted by sliding the bundle of optical fibres 8 in and out of the carrier 6 to provide optimal focussing of the incident light beam in the eye's pupillary plane 30.

The arrangement shown in FIG. 10 is similar to that of FIG. 9 but, in this case, the convergent lens 33 is provided in the carrier 6 between the illumination optical fibre 9 and the contact lens 1 rather than on the end of the fibre 9. As indicated diagramatically in FIG. 2A, a converging lens may, in fact, be provided at any position between the light source and the contact lens so long as it is arranged to focus light substantially in the pupillary plane of the eye. If desired, the optical system may comprise a plurality of lenses mounted on the light source, within the carrier 6 or on the contact lens 1 or any combination thereof to focus light in the pupillary plane.

Figure 11:
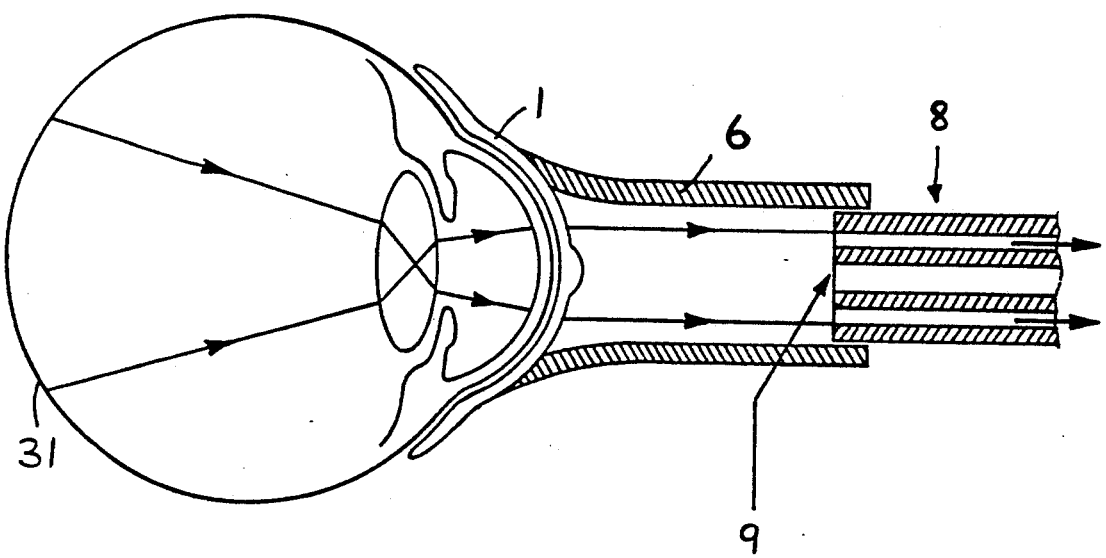
FIG. 11 is a corresponding view showing the path of light rays showing the limits of the field of view of the retina as seen by the light receiving means.

FIG. 11 illustrates the limiting light rays of diffusely reflected light from the retinal area received by the paraxial optical fibres 10 which then transmit the light to photodiodes or other light sensing means (not shown).

As described above, in any of these arrangements, the illuminating optical fibre may be replaced by a light emitting diodes or other light emitting means and the receiving optical fibres 10 may be replaced by miniature photodiodes, charged couple devices or other light sensing means. In each case, the light emitting and light receiving means would be provided with electrical connections to enable them to be connected to a power source and other electrical equipment.

The first optical system may thus be used to measure changes in the reflectance/absorbance of the blood vessels of the retina. Any combination of monochromatic lights or white light, as well as wave-lengths in the infra-red and ultra-violet spectra can be used. Specific, selected wavelengths permit optimal discrimination of the various blood components. In this way, it is, for instance, possible to provide an accurate measurement of the oxygen saturation of the retinal blood flow and, as this is closer to cerebral blood flow than the toe, finger or ear blood flow previously measured, it provides a more accurate assessment of blood delivered to the brain.

The spectrophotometric system described above may also be used for fluo-spectrophotometric analysis in which the retina is irradiated with one wavelength and it emits light of a different wavelength which is detected by the optical system. Most natural substances have auto-fluorescent properties. Fluorescent dies can also be used as appropriate.

As indicated above, this system also enables the device to monitor pulse rate by measuring changes in light absorbance/reflectance of blood vessels on the retina between diastole and systole.

The measurement of the retinal blood flow also gives an indication of cerebral blood flow as the retina and its blood supply are part of the brain and changes in retinal blood flow give an indication of changes in cerebral blood flow as well as changes in the cardiac output.

It is also possible to calculate changes in the resistance to blood flow using Ohm's Law and so provide another measure of the depth of anaesthesia.

Such measurements of cardiovascular and respiratory functions are always monitored in intensive and coronary care units as well as in any unconscious patient.

Another of the functions which can be monitored using the first optical system described above is the change in the saturation of haemoglobin, both adult and foetal, with various chemicals over time; for instance of oxygen (oxyhaemoglobin), carbon dioxide (carboxyhaemoglobin), haemoglobin without any gases (reduced haemoglobin) and sulphur (methaemoglobin) or any of the other haemoglobins.

A measurement of the percentage saturation of haemoglobin enables the haemoglobin dissociation curve to be calculated and so provide real time monitoring of this curve as well as changes in the curve with time.

It is also possible to measure in vivo abnormal haemoglobins such as HbS which causes sickle cell disease. If characteristic absorbance/reflectance spectra for each of the abnormal haemoglobins are defined, these can be held in a computer memory and then compared with in vivo measurements and their changes with time can be monitored.

It is also possible to use the device for real-time monitoring of all the many and varied biochemical substances found in the blood, For example, bilirubin has a specific light absorbance/reflectance spectrum as do other chemicals found in the blood, including the many and varied amino-acids and proteins. The limiting factor is, of course, the degree of difference between the absorbance/reflectance spectra for each of these chemicals.

If the absorbance/reflectance spectra of drugs, chemicals and their metabolites are known, it will also be possible to monitor real time changes in the blood/plasma concentration of these as they are administered to a patient. The characteristic curves of spectral absorbance/reflectance can be held in a computer memory for automatic comparison with the test data.

Selected wavelengths in the infra-red may also be used to illuminate the retina and the amount they are absorbed/reflected used to provide a measure of the carbon dioxide pressure in the blood.

It is also possible to use the absorbance/reflectance of light from the retina to monitor in real time all biochemical changes occurring in the cells of the retina, for example, cellular respiration of the retina. It is also possible to combine the measurement of fluorescence with that of absorbance/reflectance to improve further the sensitivity of the system. Measurement of the biochemical activity of retinal cells provides an indirect measurement of the biochemical activity of the brain and so provides a measure of the oxygen demand and utilisation thereof.

PUPILLOMETRY

Figure 5:
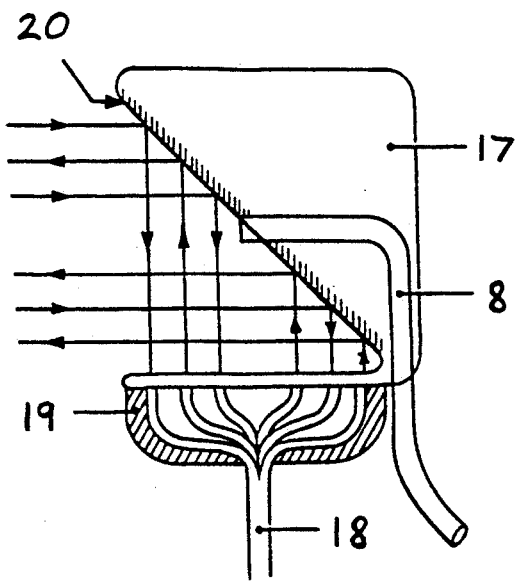
FIG. 5 is a cross-sectional view corresponding to FIG. 2 showing an embodiment of a second optical system of the invention used with the a scleral contact lens for infra-red pupillometry.
Figure 6:
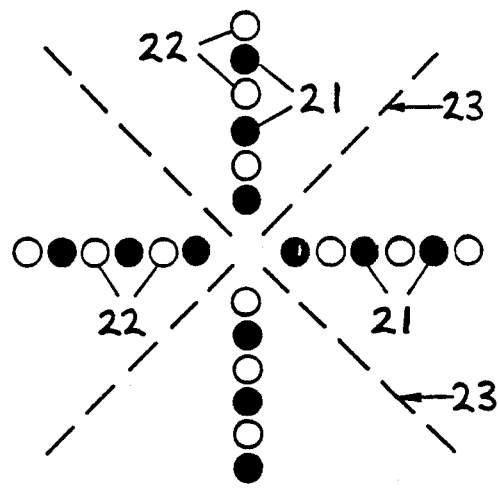
FIG. 6 is an end view of part of the second optical system shown in FIG. 5.

FIG. 5 shows components of a second optical system that may be attached to the carrier 6. The second optical system is arranged to direct light towards the pupil and iris of the eye and to receive light reflected therefrom. In the illustrated arrangement, the second optical system comprises a further coherent fibre optic bundle 18 the ends of which are arranged in a cruciform array as shown in FIG. 6. An outer protective casing 19 of PMMA or other similar material secures the bundle 18 onto an optical mount on the side of the carrier 6. A mirror 20 is provided in the carrier 6 inclined at an angle of 45 degrees so that light from the bundle 18 is reflected towards the eye through the optical portion 2 of the scleral contact lens 1 and so that light returning from the eye is reflected back to the ends of the fibres arranged in the cruciform array.

The array of fibres is, in fact, made up of two interlaced coherent arrays, a first array 21 (shown shaded) for illumination and a second array 22 (shown unshaded) attached to a charged coupled device (CCD) detector (not shown) for receiving light reflected from the eye. As shown in FIG. 6, no fibre is necessary in the centre of the array.

In use, infra-red light is passed to the first array of fibres 21 and is directed at the iris of the eye by the mirror 20 and the optical portion 2 of the contact lens 1. Depending on the size of the pupil, the light from a particular fibre either passes through the pupil into the eye where it is absorbed or is reflected by the iris and transmitted back to the second array of fibres 22 by the optical portion 2 of the lens 1 and the mirror 20. The CCD detector measures the intensity of any light received by the fibres in the second array 22. The diameter of the pupil can thus be measured by determining which of the second array of fibres 22 receives light reflected from the eye. If the pupil is large, only the outermost fibres will receive light reflected from the iris whereas if the pupil is small all but the innermost fibres will receive reflected light.

The illustrated array of fibres senses the size of the pupil across two diameters and the array preferably includes further fibres arranged across other diameters of the eye, e.g. along the dotted lines 23 shown in FIG. 6. Other forms of array could also be used, for instance a series of concentric rings with alternate fibres in each ring directing light towards the eye and detecting light reflected therefrom. The resolution of the pupil diameter is a function of the number of fibres across the array. It would also be possible to use the same fibres as both illuminating means for directing light towards the eye and receivers for receiving light reflected therefrom.

As for the spectrophotometric optical system described above, the light input optical fibres may be replaced by an array of discrete light emitting means, such as light emitting diodes, and the light receiving fibres may be replaced by an array of discrete light sensing means, such as photodiodes.

In an alternative arrangement (not shown), the second optical system may be provided without the first optical system. In this case, the lenticular 3 or other lens system may be omitted and the first and second arrays 21 and 22 of fibres arranged in the support 17 in place of the optical fibre bundle 8 so as to direct infra-red light towards the eye without the need for the mirror 20.

It is possible to monitor continuously the depth of anaesthesia by measuring the dilation of the pupil using the second optical system described above, the reflected infra-red light being used to measure the area of the pupil. Observation of changes in pupil size is the original way of clinically assessing the depth of anaesthesia and is the bench-mark against which all other techniques are measured. It is also possible to measure the pupillary light response as an assessment of the depth of anaesthesia.

FLUID MEASUREMENTS

As mentioned above, the haptic scleral contact lens 1 is provided with means for supplying artificial tears to the eye to prevent the cornea from becoming dry. This provides another way of measuring blood pressure and pulse rate since the pressure within the eye varies as the blood vessels therein expand and contract with each pulse. The liquid interface between the haptic shell 1 and the cornea of the eye acts as a pressure transducer for sensing these pressure changes. The pressure changes in this interface are transmitted to the liquid within the tubes 5 connected to the apertures 4. Thus, by using a closed system connected to the tubes 5A and 5B with monitoring apparatus (not shown) such as a pressure sensor, it is possible to measure pressure changes or movement of the liquid within the tubes 5 to provide a measurement of arterial blood pressure and pulse rate.

Changes in the hydrogen ion concentration (pH) of artificial tears supplied to the eye through the tubes 5A and 5B in a closed system can also be measured. The pH of natural tears produced by the eye is related to pH changes in the blood and as these mix with the artificial tears supplied through the tubes 5, the pH of the fluid withdrawn from the tubes 5 can be measured by colorimetry or a pH electrode to monitor these changes.

The volume of natural tears is also related to the depth of anaesthesia and this can also be monitored by measuring the changes in the volume of fluid within the tubes with a volumetric measure.

ELECTROPHYSIOLOGY

Figure 7A:
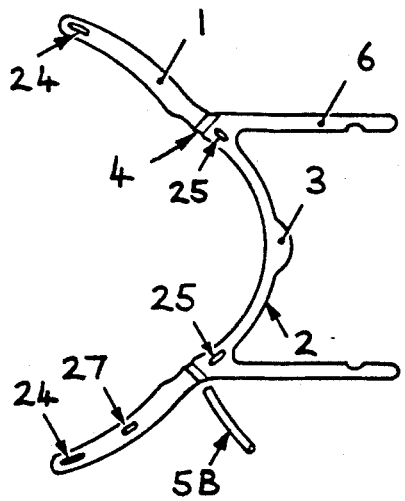
FIGS. 7A, B and C are further views of the contact lens showing electrodes used therewith.

Two sets of electrodes are provided on the scleral contact lens 1, one to apply electrical stimulation to the extra-ocular muscles or to record the electrical activity therefrom, the other to detect electrical changes in the retina of the eye. These electrodes are shown in FIG. 7.

Figures 7B, 7C:
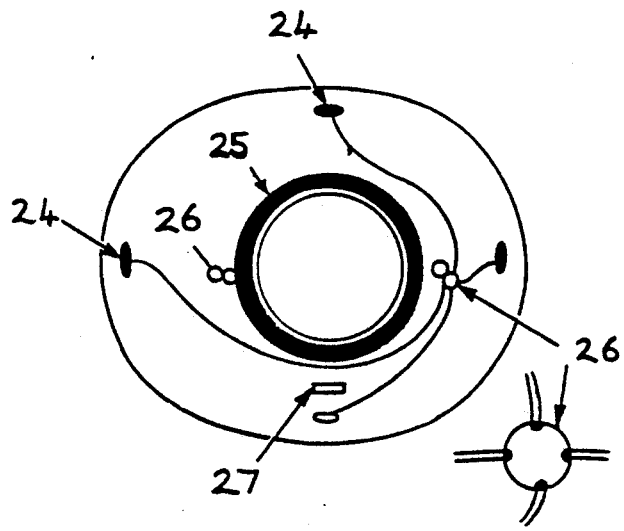

The first set comprises electrodes 24 of gold or other suitable conducting material embedded in the haptic portion of the lens 1 at points around its periphery. The electrodes 24 are embedded in the haptic portion between 6 mm and 10 mm from the center of the optical portion 3 so as to lie over the recti muscles insertions when the lens 1 is placed on the eye. The second set comprises a ring electrode 25, again preferably of gold, extending around the optical portion 2 of the lens 1. Connections to the two sets of electrodes 24 and 25 are provided by electrode pin contacts (not shown). Screened connections from the electrodes 24 and 25 extend towards sockets 26 in the haptic lens 1 as shown in FIG. 7B where they connect with the contacts provided on the pin contacts inserted therein. The enlarged view in FIG. 7C shows the separate contacts within each socket 26.

The first set of electrodes 24 are used to record the activity of the eye muscles to provide an electromyogram (EMG). The second set of electrodes 25 can be used in connection with a conventional electroretinograph (ERG).

The lateral rectus muscle may be stimulated percutaneously and the resultant EMG recorded via the electrodes 24. Any significant contraction of the lateral rectus muscle may be measured by changes in electrical potentials using a further electrode (not shown) for instance attached to the face above the eye. It is thus possible to use the standard train of four stimulation to measure the degree of muscle relaxation with this system and so monitor the degree of muscle paralysis.

As mentioned above, the device shown in FIG. 7 may also be used to measure potential changes in the retina in the same manner as a conventional electroretinogram. However, the light used to stimulate the retina may be provided by the first optical system shown in FIGS. 2-4 or FIGS. 8-11 rather than a separate, external light source.

Electrodes placed elsewhere on the head may also be used to record visual evoked responses in a conventional manner but using the first optical system described above to provide direct stimulation of the retina so allowing peroperative visual evoked potentials to be recorded because the amount of light reaching the retina is independent of pupil size.

The electrical activity of the heart can also be recorded by suitable electrodes placed anywhere on the body so either of the electrodes 24 or 25 provided on the haptic portion of the lens 1 may also be used in conjunction with other electrodes to record an ECG.

TEMPERATURE SENSING

The lens 1 may also be provided with a thermistor (thermo-couple) or infra-red sensor 27 (see FIGS. 1A and 7B) to measure the temperature of the eye.

Temperature measurements are necessary during anaesthesia to diagnose malignant hyperexia which is an unusual but potentially fatal condition. The temperature is also important in calculating the amount of oxygen available to the tissues (e.g. the brain) as it effects the haemoglobin dissociation curve.

It will be appreciated that the contact lens 1 locates and supports the device on the eye and, when using discrete light emitting and discrete light receiving means as described above, the contact lens is able to support the optical system and other sensors attached thereto. There is, therefore, no need to hold or support larger or heavier equipment in front of the eye. Instead, optical fibres or electrical wires transmit light and/or information between the device and a remote light source and remote light sensing means which may be mounted alongside or form part of analysis and display equipment located at the patient's bedside or beside the operating table.

ANALYSIS AND DISPLAY EQUIPMENT

The analysis and display equipment connected to the various sensors of the device is arranged to provide a variety of different displays and outputs.

The importance of real-time monitoring during anaesthesia and in medicine generally is to record changes in a patient's physiological state with time. The device will enable the doctor to monitor heart rate, blood pressure (both of which are important in cardiac output), and the amount of oxygen being carried by the blood with the saturation percentage. Thus, the major components of oxygen delivery, transport and content can be monitored. The Hb dissociation curve can be calculated from the data obtained and any change noted in addition to changes consequent to any clinical intervention, the time of which may also be recorded. A statistical analysis can be automatically carried out to calculate the mean and the standard deviation of each feature measured as well as changes in measurements over time to provide an alert or signal an alarm system if significant changes are recorded.

The pupil diameter and the electroretinogram are both measures of the depth of anaesthesia and real-time monitoring enables an indication to be given if this is becoming too deep or too light.

The EMG provides real time monitoring of the degree of muscular paralysis which is particularly important during microscopic surgery.

Electronic control means are provided to monitor, display and record signals provided by each of the different monitoring systems described above. The electronic equipment may be arranged to provide a wide variety of information depending on the intended use and the requirements of the doctor. Further details of the construction and operation of the electronic control means is not provided since a wide variety of systems will be apparent to those skilled in the art or are already available.

Features which may be displayed on the instrument include: the saturation percentage of oxygen, the haemoglogin dissociation curve, pupil diameter, pulse rate, blood pressure, temperature and pH as well as the displays conventionally provided by an electrocardiograph (ECG), electroretinograph (ERG), and electromyograph (EMG). The displays may be presented in graphic or numerical format (or both).

All this information is stored and a hard copy may be produced at the end of the procedure for placing in the patient's records.

It will be appreciated that the device described above may be used in a wide variety of diagnostic, monitoring and examination techniques which may be carried out in vivo, non-invasively and in real time. In view of the small size and lightness of the optical system carried by the scleral contact lens, the device can be conveniently located and supported on the eye of the patient and simply connected to other monitoring equipment by the appropriate optical and/or electrical connections. No heavy or bulky equipment needs to be positioned or supported in front of the eye so the device can be used to monitor a patient's condition, e.g. on an operating table, without obstructing access to the patient.

INDUSTRIAL APPLICABILITY

The device described above can be manufactured for use in hospitals and surgeries. The disposable component described may be manufactured and supplied as a spare part for use with such devices. The methods described may be used by the medical profession to monitor human or animal bodily functions.

We claim:

1. A device for use in real-time monitoring of human or animal bodily functions in vivo comprising:
    a scleral contact lens for locating and supporting the device on an eye including a pupil having a size determined by dilation of the pupil, a retina and an iris, of a human or animal; and a first optical system supported by the contact lens having at least one discrete light input means and at least one discrete light receiving means, wherein the light input means is arranged to direct light through the contact lens and the pupil of the eye so as to illuminate at least a portion of the retina of the eye substantially independently of the pupil size and the light receiving means is positioned so as to receive light returning through the contact lens directly from a portion of the retina which is illuminated directly by the light input means.

2. A device as claimed in claim 1 in which said at least one discrete light input means comprises an optical fibre for transmitting light from a remote light source to the device.

3. A device as claimed in claim 2 in which the first optical system is arranged such that said optical fibre may function both as light input means and light receiving means.

4. A device as claimed in claim 1 in which said at least one discrete light receiving means comprises an optical fibre for transmitting light from the device to remote light sensing means.

5. A device as claimed in claim 1 in which said at least one discrete light input means comprises light emitting means carried by the device and provided with electrical connections for connecting it to a power source.

6. A device as claimed in claim 1, in which said at least one discrete light receiving means comprises light sensing means carried by the device and provided with electrical connections for connecting it to other electrical means.

7. A device as claimed in claim 1 wherein the pupil defines a plane and an optical axis arranged such that the first optical system focusses light substantially in the plane of the pupil of the eye and substantially along the optical axis of the pupil.

8. A device as claimed in claim 7 with a light source and light sensing means arranged to monitor an intensity of light of a selected wavelength returning from the retina of the eye.

9. A device as claimed in claim 7 with a light source and light sensing means arranged to determine an intensity of light of different wavelengths returning from the retina whereby an absorbance/reflectance characteristic of the retina can be determined.

10. A device as claimed in claim 1 comprising a second optical system arranged to direct light towards the eye and to receive light reflected from the iris of the eye.

11. A device as claimed in claim 10 wherein the pupil defines a plane and an optical axis and the second optical system comprises an array of discrete light input means for providing light and for directing that light towards the eye at a series of different distances from the optical axis and an array of discrete light receiving means for receiving light reflected from the iris of the eye at a series of different distances from the optical axis.

12. A device as claimed in claim 11 with a light source and light sensing means arranged to determine which of the array of discrete light receiving means receives light reflected from the iris whereby dimensions of the pupil can be determined.

13. A device as claimed in claim 1 in which the contact lens is disposable and is provided with mounting means for detachably securing at least part of the optical system thereto.

14. A device as claimed in claim 1 in which the eye has a cornea and apertures are provided in the contact lens for passing fluid through the lens to the cornea of the eye.

15. A device as claimed in claim 14 comprising fluid supply means for passing the fluid to the eye and receiving the fluid returning there from via said apertures and fluid sensing means for sensing at least one of the following: pressure changes within the fluid, movement of the fluid, a volume of fluid received from the eye and a pH of fluid received from the eye.

16. A device as claimed in claim 1 in which the contact lens defines a periphery and is provided with electrodes in positions adjacent the periphery of the contact lens so that when the contact lens is positioned on the eye, the electrodes lie over and can be used to stimulate recti muscle insertions of the eye.

17. A device as claimed in claim 1 in which the contact lens is provided with temperature sensing means for sensing temperature of the eye.

18. A disposable component of a device for real-time monitoring of human or animal bodily functions in vivo, the component comprising a scleral contact lens for locating and supporting the device on an eye including a pupil having a size determined by dilation of the pupil, a retina and an iris, of a human or animal and mounting means on the contact lens configured for detachably mounting and supporting an optical system on the lens in such a manner that, when mounted thereon, the optical system is positioned to direct light through the contact lens and the pupil of the eye so as to illuminate the retina of the eye substantially independently of the pupil size and to receive light returning through the contact lens from that portion of the retina illuminated by the optical system.

19. A method of real-time monitoring of human or animal bodily functions in vivo comprising
using a scleral contact lens for locating and supporting a real-time monitoring device on an eye including a pupil having a size determined by dilation of the pupil, a retina and an iris, of a human or animal; supporting an optical system by the contact lens, the system having at least one discrete light input means and at least one discrete light receiving means, using the light input means to direct light through the contact lens and the pupil of the eye so as to illuminate at least a portion of the retina of the eye substantially independently of the pupil size and positioning the light receiving means to receive light returning through the contact lens directly from that portion of the retina which is illuminated directly by the light input means.

20. A device for use in real-time monitoring of human or animal bodily functions in vivo comprising:
a scleral contact lens for locating and supporting the device on an eye including an iris, of a human or animal, the eye having a pupil defining an optical axis, and an optical system supported by the contact lens arranged to direct light towards the eye and to receive light reflected from the iris of the eye, characterized in that the optical system comprises an array of discrete light input means for providing light and for directing that light towards the eye at a series of different distances from the optical axis and an array of discrete light receiving means for receiving light reflected from the iris of the eye at a series of different distances from the optical axis.

21. A device as claimed in claim 20 with a light source and light sensing means arranged to determine which of the array of discrete light receiving means receives light reflected from the iris whereby dimensions of the pupil can be determined.

22. A method of carrying out spectrophotometric analysis of a retina of an eye comprising the steps of:
using a scleral contact lens for locating and supporting a real-time monitoring device on an eye including a pupil having a size determined by dilation of the pupil, a retina and an iris, of a human or animal;
supporting an optical system by the contact lens, the system having at least one discrete light input means and at least one discrete light receiving means;
using the light input means to direct light of a plurality of wavelengths from a light source through the contact lens and the pupil of the eye so as to illuminate at least a portion of the retina of the eye substantially independently of the pupil size,
positioning the light receiving means so as to receive light returning through the contact lens from a portion of the retina which is illuminated directly by the light input means;
using light sensing means to determine an intensity of light of different wavelengths received by the light receiving means, and
determining an absorbance/reflectance characteristic for the retina therefrom.

23. A method of determining dimensions of a pupil of an eye of a patient comprising the steps of:
using a scleral contact lens for locating and supporting a real-time monitoring device on an eye including a pupil and an iris;
supporting an optical system by the contact lens, the optical system comprising an array of discrete light input means for directing light towards the iris of the eye at a series of different distances from an optical axis and an array of discrete light receiving means for receiving light reflected from the iris of the eye at a series of different distances from the optical axis;
supplying light via a light source and the array of discrete light input means towards the eye;
determining, with light sensing means, which of the array of light receiving means receives light reflected from the iris with the dimensions of the pupil being determined therefrom.

* * * * *